United States Patent [19]

Evans et al.

[11] Patent Number: 4,647,670
[45] Date of Patent: * Mar. 3, 1987

[54] TRANS-3,4-DIHYDRO-2,2-DIMETHYL-6-NITRO-4-(2-OXO-PYRROLIDINYL)2H-1-BENZOPYRAN-3-OL

[75] Inventors: John M. Evans, Roydon; Robin E. Buckingham, Welwyn Garden; Kenneth Willcocks, Harlow, all of England

[73] Assignee: Beecham Group p.l.c., England

[*] Notice: The portion of the term of this patent subsequent to May 1, 2001 has been disclaimed.

[21] Appl. No.: 679,685

[22] Filed: Dec. 10, 1984

Related U.S. Application Data

[62] Division of Ser. No. 487,098, Apr. 21, 1983, Pat. No. 4,510,152.

[30] Foreign Application Priority Data

Apr. 28, 1982 [GB] United Kingdom ............... 8212358

[51] Int. Cl.$^4$ ........................................... C07D 405/04
[52] U.S. Cl. ................................................... 548/525
[58] Field of Search ......................................... 548/525

[56] References Cited

U.S. PATENT DOCUMENTS 4,446,113 5/1984 Evans et al. .................. 548/525 X Primary Examiner—Richard A. Schwartz
Attorney, Agent, or Firm—Jacobs & Jacobs

[57] ABSTRACT

Compounds of formula (I):

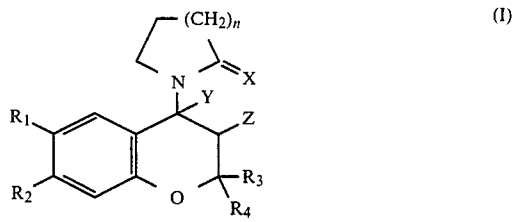

wherein the various substituents are defined hereinbelow, having anti-hypertensive activity.

1 Claim, No Drawings

TRANS-3,4-DIHYDRO-2,2-DIMETHYL-6-NITRO-4-(2-OXO-PYRROLIDINYL)2H-1-BENZOPYRAN-3-OL

CROSS-REFERENCE

This is a continuation of Ser. No. 487,098 filed Apr. 21, 1983, now U.S. Pat. No. 4,510,152.

The present invention relates to novel chromenes and chromans having pharmacological activity, to a process for preparing them, to pharmaceutical compositions containing them, and to their use in the treatment of mammals.

U.S. Pat. No. 4,110,347 discloses compounds having blood pressure lowering activity which are of formula (A'):

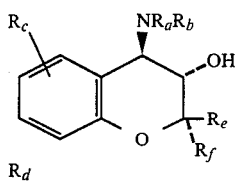

and acid addition salts thereof wherein $R_a$ is a hydrogen atom or a $C_{1-9}$ hydrocarbon group optionally substituted by a hydroxyl or $C_{1-6}$ alkoxyl group; $R_b$ is a hydrogen atom or $C_{1-6}$ alkyl group, or $NR_aR_b$ is a 3–8 membered heterocyclic group optionally substituted by one or two methyl groups; $R_c$ is a hydrogen or halogen atom or a $C_{1-6}$ alkyl, $C_{2-6}$ alkenyl, $C_{1-6}$ alkoxy, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $AOR_g$, $ASR_g$, $ASO_2R_g$, $ANHR_g$, $ANR_gCOR_h$, $ANR_gSO_2R_h$ or $ANR_gCO_2R_h$ group, in which A is an alkylene group of 1–4 carbon, $R_g$ is an alkyl group of 1–4 carbon atoms, and $R_h$ is an alkyl group of 1 to 4 carbon atoms; and $R_d$ is a hydrogen or halogen atom or methyl or methoxy, or $R_c$ together with $R_d$ forms a —C=CH—CH=CH—, —NH—CH=CH—, —CH$_2$—CH$_2$—CH$_2$—CH$_2$— or —CH$_2$—CH$_2$—CH$_2$—CO— system; $R_e$ is a hydrogen atom or a $C_{1-6}$ alkyl or phenyl group; and $R_f$ is a hydrogen atom or a $C_{1-6}$ alkyl or phenyl group.

U.S. Pat. No. 4,251,537 discloses compounds having useful anti-hypertensive activity, which are of formula (B'):

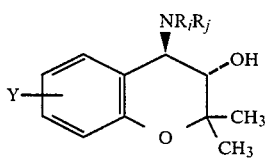

wherein $R_i$ is a hydrogen atom or an alkyl group of up to 4 carbon atoms optionally substituted by a chlorine or bromine atom or by a hydroxyl group or by an alkoxyl group of up to 4 carbon atoms or by an acyloxy group of up to 4 carbon atoms and $R_j$ is a hydrogen atom or an alkyl group of up to 4 carbon atoms or $R_i$ is joined to $R_j$ so that together with the nitrogen atom to which they are attached they form a 5-, 6- or 7-membered heterocyclic ring which is optionally substituted by methyl; Y is a group $COR_k$, $CO_2R_k$, $SOR_k$, $SO_2R_k$, $SOOR_k$, $SO_2OR_k$, $CH(OH)R_k$, $C(R_k)$=NOH, $C(R_k)$=NNH$_2$, $CONH_2$, $CONR_lR_m$, $SONR_lR_m$ or $SO_2NR_lR_m$ where $R_k$ and $R_l$ are each independently a hydrocarbon group of up to 8 carbon atoms or such a group inertly substituted by a chlorine or bromine atom or by a hydroxyl group or by an alkoxyl group of 1–4 carbon atoms or by an acyloxy group of up to 4 carbon atoms or by 3 fluorine atoms attached to the same carbon atom and $R_m$ is a hydrogen atom or an alkyl group of up to 4 carbon atoms; and salts thereof and O-acyl derivatives thereof wherein the O-acyl moiety contains up to 18 carbon atoms.

European Patent Publication No. 9912 describes antihypertensive compounds of formula (C'):

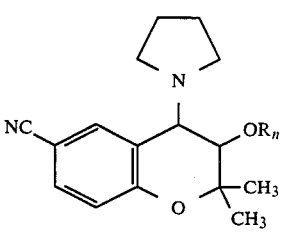

wherein the pyrrolidino and $OR_n$ moieties are trans and wherein $R_n$ is a hydrogen atom, an alkyl group of 1 to 3 carbon atoms or an acyl group of 1 to 8 carbon atoms; or a pharmaceutically acceptable acid addition salt thereof.

European Patent Publication No. 28449 describes compounds having blood pressure lowering activity, with low levels of unwanted cardiac effects, which compounds are of formula (D'):

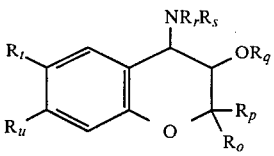

$R_o$ is a hydrogen atom or a lower alkyl group;
$R_p$ is a hydrogen atom or a lower alkyl group;
$R_q$ is a hydrogen atom or a lower alkyl group;
$R_r$ is a hydrogen atom or a lower alkyl group;
$R_s$ is a lower alkyl or a substituted alkyl group;
or $R_4$ and $R_5$ are joined so that together with the nitrogen atom to which they are attached they form a 5-, 6- or 7-membered ring optionally containing an oxygen or sulphur atom;
$R_t$ is an electron withdrawing group;
$R_n$ is an electron donating group; and the $NR_rR_s$ and $OR_q$ moieties are trans.

European Patent Publication No. 28064 describes compounds having blood pressure lowering activity, with low levels of unwanted cardiac effects, which compounds are of formula (E'):

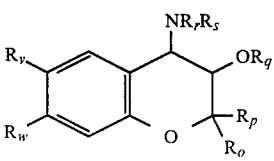

and salts and pro-drugs thereof, wherein:

$R_o$ $R_p$ $R_q$ $R_r$ and $R_s$ are as defined for formula (D'), and $R_v$ is an electron donating group and $R_w$ is an electron withdrawing group; and the $NR_rR_s$ and $OR_q$ moieties are trans.

A class of chromenes and chromans have now been discovered and have been found to have blood pressure lowering activity.

Accordingly, the present invention provides a compound of formula (I):

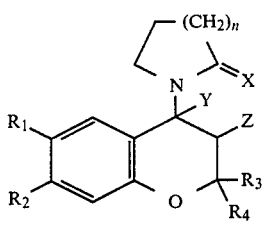
(I)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
X is oxygen or sulphur;
Y and Z are each hydrogen or together represent a bond;
n is 1 or 2; when one or the other of $R_1$ and $R_2$ is an amino or an amino-containing group, a pharmaceutically acceptable salt thereof.

When one of $R_1$ and $R_2$ is hydrogen, the other is favourably selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro cyano or chloro. In particular, when one of $R_1$ and $R_2$ is hydrogen, the other is preferably nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Favourably, $R_3$ and $R_4$ are both alkyl having from 1 to 4 carbon atoms including methyl ethyl, n- and iso-propyl. They are both methyl or ethyl, preferably both methyl.

X is preferably oxygen.

Y and Z together preferably represent a bond.

It is preferred that the compounds of formula (I) are in substantially pure form.

There is a group of compounds within formula (I) wherein one of $R_1$ and $R_2$ is hydrogen and the other is selected from the class of $C_{1-6}$ alkoxycarbonyl, $C_{1-6}$ alkylhydroxymethyl, nitro, cyano or chloro, or one of $R_1$ and $R_2$ is nitro or cyano and the other is amino optionally substituted by one or two $C_{1-6}$ alkyl or by $C_{2-7}$ alkanoyl; $R_3$ is hydrogen or $C_{1-4}$ alkyl; $R_4$ is $C_{1-4}$ alkyl; X is oxygen; Y and Z together represent a bond and the remaining variables are as defined in formula (I).

It will be appreciated that there is a favourable sub-group of compounds within formula (I) of formula (II):

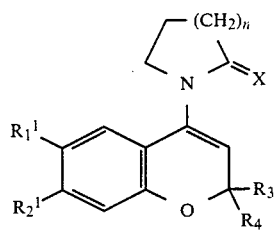
(II)

wherein one of $R_1^1$ and $R_2^1$ is hydrogen and the other is cyano or nitro and the remaining variables are as defined in formula (I).

Suitable and preferred values for the variables are as described under formula (I).

From the aforesaid it will be appreciated that there is a preferred compound within formula (II) of formula (III):

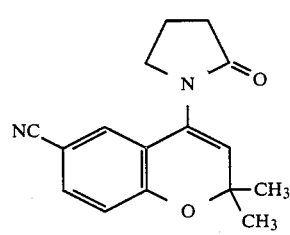
(III)

There is a further sub-group of compounds within formula (I) of formula (IV):

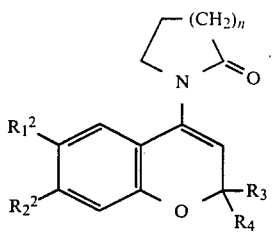

wherein:
one of $R_1^2$ and $R_2^2$ is cyano or nitro and the other is substituted amino as defined and the remaining variables are as defined in formula (I).

Favourably $R_1^2$ is cyano or nitro and $R_2^2$ is amino. Suitable and preferred values for the remaining variables are as described under formula (I).

The present invention also provides a process for the preparation of a compound of formula (I) which process comprises the dehydration of a compound of formula (V) or a metal salt thereof:

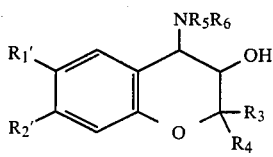

wherein:
$R_1'$ and $R_2'$ are $R_1$ and $R_2$ respectively or a group or atom convertible thereto;
$R_5$ and $R_6$ together form $—(CH_2)_{n+2}CX—$; or $R_5$ is hydrogen and $R_6$ is $—(CH_2)_{n+2}CX^1L_1$; wherein $X^1$ is oxygen and $L_1$ is a leaving group; and $R_3$ and $R_4$ are as defined in formula (I); and thereafter optionally converting $R_1'$ or $R_2'$ to $R_1$ or $R_2$ respectively; optionally thiating a $C=X^1$ carbonyl group, and optionally reducing a Y—Z bond and, when one of $R_1$ and $R_2$ in the compound of formula (I) is an amino containing group, optionally forming a pharmaceutically acceptable salt thereof.

The dehydration may be carried out using a suitable dehydrating agent such as sodium hydride in an inert solvent such as dry tetrahydrofuran at reflux temperatures.

The cyclisation of $R_5/R_6$ when $R_6$ is $—(CH_2)_{n+2}CX^1L_1$, takes place spontaneously at elevated temperatures. $L_1$ is a group readily displaceable by a secondary amino nucleophile as described in formula (VI).

Examples of optional conversions of $R_1$ or $R_2$ in a compound of formula (I) into another $R_1$ or $R_2$, as defined hereinbefore, are generally known in the art of aromatic chemistry. For example, an α-hydroxyethyl group may be converted into acetyl by oxidation, a chloro atom may be converted into an amino group by amination, an amino group may be converted into amino substituted by one or two $C_{1-6}$ alkyl or by $C_{2-7}$ alkanoyl, or an hydrogen atom may be converted into a nitro group by nitration.

It is however, preferred that conversions of $R_1$ and $R_2$ are carried out at an earlier stage.

The thiation reaction is preferably carried out with conventional thiation agents, such as hydrogen sulphide, phosporous pentasulphide and Lawesson's reagent (p-methoxyphenylthiophosphine sulphide dimer).

The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is carried out at temperatures from room temperatures to reflux in a dry solvent, such as toluene or methylene chloride.

When X is sulphur and $R_1$ or $R_2$ is a carbonyl-containing group in formula (I), then it is preferred to use the corresponding compound of formula (V), wherein $R_1'$ or $R_2'$ is a protected carbonyl-containing group, in the thiation reaction, and afterwards to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

Compounds of the formula (I) wherein X is sulphur are preferably prepared by thiation of the compounds of formula (I) wherein X is oxygen.

The reduction of a Y—Z bond may be carried out by conventional catalytic hydrogenation using Palladium on charcoal.

When one of $R_1$ and $R_2$ in the compound of formula (I) so obtained is an amino or an amino-containing group, the optional formation of a pharmaceutically acceptable salt thereof may be carried out in accordance with conventional procedures.

The compound of fomula (V) wherein $R_5$ and $R_6$ together form $—(CH_2)_{n+2}CO—$ may be prepared by cyclising a compound of formula (VI), or metal salt thereof:

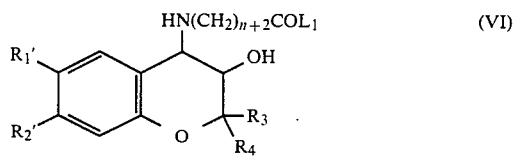

wherein $R_1'$, $R_2'$, $R_3$ and $R_4$ and n are as hereinbefore defined, the substituted amino group is trans to the $OH_5$ group, and $L_1$ is a leaving group.

The leaving group ($L_1$) is a group that is displaceable by a secondary amino nucleophile. Preferred examples of such groups include hydroxy and, in particular, $C_{1-4}$ alkoxy, such as ethoxy.

The cyclisation is normally carried out by heating the compound of formua (VI) under reflux in an inert solvent, such as xylene or toluene.

When a metal salt of formula (VI) is used, the sodium salt is preferred.

A compound of formula (VI) may be prepared by reacting a compound of formula (VII):

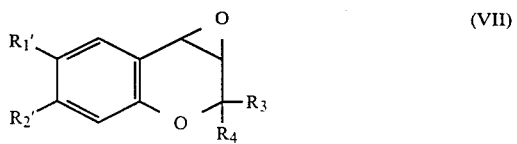

wherein $R_1'$ and $R_2'$ and $R_3$ and $R_4$ are as hereinbefore defined with a compound of formula (VII):

$$H_2N-(CH_2)_{n+2}-COL_1 \qquad (VIII)$$

wherein n and $L_1$ are as hereinbefore defined.

The reaction is normally carried out in a solvent at low, medium or high temperature. The solvent may be an alcohol, such as methanol or ethanol.

When $L_1$ is hydroxy the reaction proceeds well if carried out in refluxing ethanol in the presence of aqueous sodium carbonate. When $L_1$ is $C_{1-4}$ alkoxy, the reaction is preferably carried out in the presence of sodium hydroxide in ethanol.

A compound of formula (VII) may be prepared, preferably in situ, by reacting a compound of formula (IX):

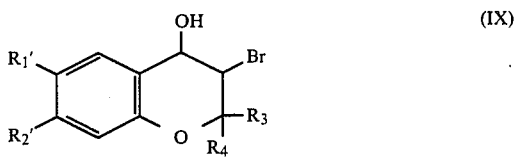

wherein $R_1'$, $R_2'$, $R_3$ and $R_4$ are hereinbefore defined and the hydroxy group is trans to the bromo atom, with a base, such as potassium hydroxide, with ether or aqueous dioxan.

Alternatively, a compound of formula (VI) may be prepared by reacting a compound of formula (X):

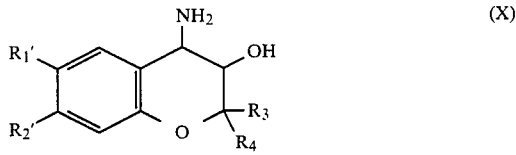

wherein $R_1'$, $R_2'$, $R_3$ and $R_4$ are as herein before defined, and the amino group is trans to the hydroxy group, with a compound of formula (XI):

$$L_2(CH_2)_{n+2}COL_1 \qquad (XI)$$

wherein n and $L_1$ are as hereinbefore defined and $L_2$ is a leaving group.

The leaving group ($L_2$) is a group that is displaceable by a primary amino nucleophile. Preferred examples of such groups include halo, such as chloro and bromo.

A compound of formula (X) may be prepared by a reaction of a compound of formula (IV) with ethanolic ammonium hydroxide solution. Alternatively, it may be prepared by reduction with zinc and hydrochloric acid of a compound of formula (XII):

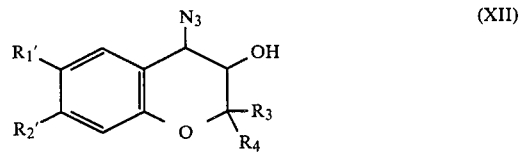

wherein $R_1'$, $R_2'$, $R_3$ and $R_4$ are as defined hereinbefore and wherein the azide group is trans to the hydroxy group.

A compound of formula (XII) may in turn be prepared from a compound of formula (VII) by reaction with sodium azide in the presence of boric acid in for example dimethylformamide.

Alternatively, a compound of formula (V) wherein X is oxygen and $R_5$ and $R_6$ together form $-(CH_2)_{n+4}CO-$ may be prepared by oxidising a compound of formula (XIII), or a metal salt thereof:

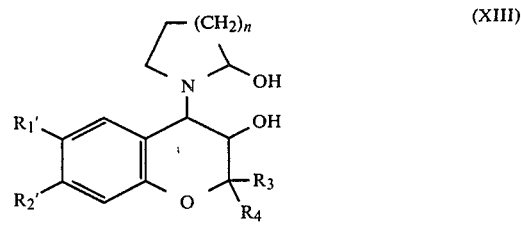

wherein $R_1'$, $R_2'$, $R_3$, $R_4$ and n are as hereinbefore defined, and wherein the lactam group is trans to the OH group.

The oxidation is preferably carried out in a solvent such as aqueous methanol with a metal periodate such as potassium periodate.

A compound of formula (XIII) may be prepared by cyclising in the presence of an acid a compound of formula (XIV):

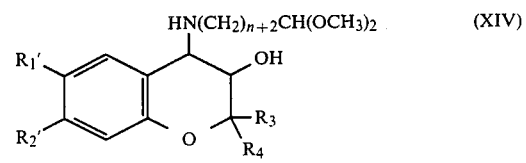

wherein $R_1'$, $R_2'$, $R_3$ and $R_4$ and n are as hereinbefore defined and wherein the substituted amino group is trans to the OH group.

A compound of formula (XIV) may in turn be prepared by reacting a compound of formula (VII) with a compound of formula (XV):

$$H_2N(CH_2)_{n+2}CH(OCH_3)_2 \qquad (XV)$$

wherein n is as hereinbefore defined.

As a further alternative, a compound of formula (V) wherein X is O and $R_5$ and $R_6$ together form $(CH_2)_{n+4}CO-$ may be prepared by reacting a compound of formula (VII) with an anion of formula (XVI):

wherein n is as hereinbefore defined.

The reaction is preferably carried out in a solvent such as dimethylsulphoxide in the presence of a base, such as sodium hydride.

A compound of formula (VII) may be prepared in situ from the corresponding compound of formula (IX). In such circumstances, it is advantageous not to add the lactam of formula (XVI) until sufficient time has elapsed for the epoxide of formula (VII) to be produced.

As a yet further alternative, a compound of formula (V) wherein X is O and $R_5$ and $R_6$ together form $(CH_2)_{n+4}CO-$ may be prepared by cyclising a compound of formula (XVII):

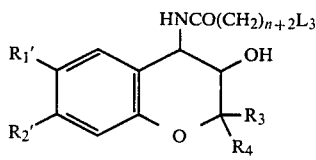
(XVII)

wherein $R_1'$, $R_2'$, $R_3$, $R_4$ and n are as hereinbefore defined and $L_3$ is a leaving group, and wherein the substituted amino group is trans to the OH group.

The leaving group ($L_3$) is a group that is displaceable by a secondary amino nucleophile adjacent a carbonyl function. A preferred example is chloro.

The cyclisation reaction is preferably carried out in a solvent such as dimethylformamide in the presence of a base, such as sodium hydride.

A compound of formula (XVII) may be prepared by reacting a compound of formula (X) with a compound of formula (XVIII):

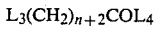
$L_3(CH_2)_{n+2}COL_4$ (XVIII)

wherein $L_3$ and n are as hereinbefore defined and $L_4$ is a leaving group.

The leaving group ($L_4$) is a group that, when adjacent a carbonyl function, is displaceable by a primary amino nucleophile.

The reaction is preferably carried out in a solvent, such as chloroform or methylene chloride, in the presence of aqueous base, such as aqueous sodium hydroxide.

In the reactions with the epoxide of formula (VII), the trans isomer is specifically formed.

In the compounds of formulae (V), (VI), (XIII), (XIV), (XVII), the OH group may, optionally be protected for example by forming a $C_{1-6}$ alkoxy or $C_{1-8}$ acyl group and subsequent deprotection may be carried out at an appropriate stage. The thiation reaction of a $C=X^1$ group is preferably carried out on a compound of formula (V) wherein the OH group is protected by a $C_{1-8}$ acyl group; such as tosyl or mesyl group and after the thiation has been carried out, to remove the $C_{1-8}$ acyl group. In this way, the use of, for example, phosphorous pentasulphide will not give rise to the thiation of the hydroxy group. If, however, the greatly preferred Lawesson's reagent is used, then there is no need to protect the hydroxy group since little, if any, hydroxy thiation takes place.

Compounds of formula (IX) are known and may be prepared in accordance with any appropriate known process, for example, by the process described in the aforementioned U.S. patents and European patent publications. Schematically, such process can be depicted thus:

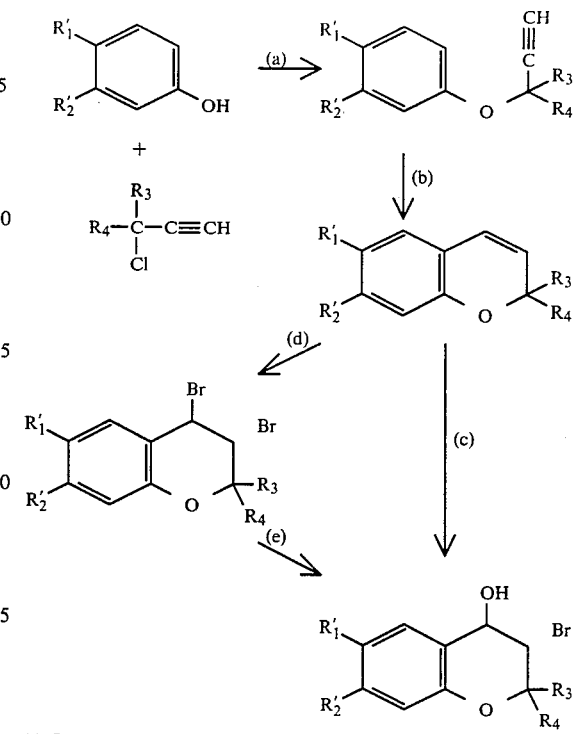

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or or (d).

It is preferred that the compounds of formula (I) are isolated in substantially pure form.

As mentioned previously, the compounds of formula (I) have been found to have blood-pressure lowering activity. They are therefore useful in the treatment of hypertension.

The present invention accordingly provides a pharmaceutical composition which comprises a compound of formula (I) and a pharmaceutically acceptable carrier. In particular, the present invention provides an anti-hypertensive pharmaceutical composition which comprises an anti-hypertensive effective amount of a compound of formula (I) and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent. They are formulated in conventional manner, for example in a manner similar to that used for known anti-hypertensive agents, diuretics and β-blocking agents.

The present invention further provides a compound of formula (I) for use in the treatment of hypertension.

The present invention yet further provides a method of treating hypertension in mammals including man, which comprises administering to the suffering mammal an anti-hypertensive effective amount of a compound of formula (I) or a pharmaceutical composition of the invention.

The following descriptions relate to the preparation of intermediates and the following examples relate to the preparation of a compound of formula (I).

DESCRIPTION 1

6-Cyano-3,4-dihydro-2,2-dimethyl-3,4-epoxy-2H-benzo[b]pyran

4-Cyanophenol (19.60 g), sodium hydroxide (9.90 g), 40% benzyltrimethylammonium hydroxide in methanol (34.50 g) and 3-methyl-3-chlorobutyne (25.50 g) were stirred in water (150 ml) and dichloromethane (150 ml) for 5.5 days at room temperature. After separation of the layers, the aqueous layer was extracted twice with chloroform, and the combined organic phase evaporated leaving a gum which was taken up in ether and washed three times with 10% sodium hydroxide solution and with water before drying over magnesium sulphate. Removal of drying agent and solvent gave a viscous liquid having absorptions in the IR (film) at 2100, 2220, 3290 cm$^{-1}$. This liquid (20.91 g) was heated in o-dichlorobenzene (40 ml) at reflux temperature for 1.5 hours under nitrogen. After distillation of the solvent the fraction boiling at 110°–114°/0.02 mmHg (16.57 g) was collected, which on standing formed a low melting solid, having an IR absorption at 2230 cm$^{-1}$. (See M. Harfenist and E. Thom, *J. Org. Chem.*, 841 (1972) who quote m.p. 36°–37°).

Addition to this 6-cyanochromene (16.50 g) dissolved in dimethyl sulphoxide (150 ml) containing water (3.24 ml) of N-bromosuccinimide (31.90 g) with vigorous stirring and cooling, followed by dilution with water and extraction via ethyl acetate gave a mixture which was boiled in acetone (300 ml) and water (100 ml) for 5 hours to hydrolyse the small amount of 3,4-dibromide present. Evaporation of solvents gave 6-cyano-trans-3-bromo-3,4-dihydro-2,2-dimethyl-2H-benzo[b]pyran-4-ol as white crystals (24.37 g). A small sample had m.p. 128°–128.5° from 60°–80° petroleum ether, nmr (CDCl$_3$) 1.43 (3H), 1.62 (3H), 7.48 (1H, exchangeable), 4.07 (1H, d, J=9), 4.87 (1H, d, J=9), 6.80 (1H, d, J=8), 7.43 (1H, q, J=8, 2), 7.78 (1H, d, J=2). Analysis calculated for C$_{12}$H$_{12}$NO$_2$Br: C, 51.07; H, 4.26; N, 4.96; Br, 28.37. Found: 50.95; H, 4.38; N, 5.03; Br, 28.39%.

The bromohydrin (24.30 g) was stirred with sodium hydroxide pellets (5.00 g) in water (250 ml) and dioxan (200 ml) for 3 hours at room temperature. The solvents were removed by distillation under high vacuum and the residue taken up in ether and washed with water and brine before drying over magnesium sulphate. Removal of drying agent and solvent and gave crude 6-cyano-3,4-dihydro-2,2-dimethyl-3,4-epoxy-2H-benzo[b]pyran (16.02 g) as a gum, having an absorption at 2230 cm$^{-1}$ in the IR and Nmr (CCl$_4$) 1.26 (3H), 1.54 (3H), 3.40 and 3.80 (each 1H, d, J=4), 6.77 (1H, d, J=8), 7.43 (1H, q, J=8, 2), 7.58 (1H, d, J=2).

DESCRIPTION 2

6-Cyano-3,4-dihydro-2,2-dimethyl-trans-4-amino-2H-benzo[b]pyran-3-ol

The title compound was prepared by stirring 6-cyano-3,4-dihydro-2,2-dimethyl-3,4-epoxy-2H-benzo[b]pyran in ethanolic ammonium hydroxide solution at room temperature until thin layer chromatography showed consumption of the starting epoxide.

DESCRIPTION 3

6-Cyano-3,4-dihydro-2,2-dimethyl-trans-4-(1-keto-4-chlorobutylamino)-2H-benzo[b]pyran-3-ol The amino chromanol (1.40 g), as obtained in Description 2, was stirred in chloroform (20 ml) and water (10 ml) containing sodium hydroxide pellets (0.26 g) at room temperature. 4-Chlorobutyryl chloride (0.72 ml) was added and the reaction stirred vigorously for 0.5 hours. Separation of the layers and washing the organic layer with water, then brine, drying over magnesium sulphate, filtration and evaporation gave the title compound as a pale yellow solid.

DESCRIPTION 4

6-Cyano-3,4-dihydro-2,2-dimethyl-trans-4-(4,4-diethoxybutylamino)-2H-benzo[b]pyran-3-ol 6-Cyano-3,4-dihydro-2,2-dimethyl-3,4-epoxy-2H-benzo[b]pyran (200 mg) and 4-aminobutyraldehyde diethylacetal (200 mg) were heated to 100°C. for 1.5 hours, a clear yellow solution forming during this time. After cooling, dilution with ether, and washing successively with water and brine, drying over sodium sulphate and evaporation, the aminoacetal was obtained as a pale yellow oil (291 mg).

DESCRIPTION 5

6-Cyano-3,4-dihydro-2,2-dimethyl-trans-4-(2-hydroxy-1-pyrrolidinyl)-2H-benzo[b]pyran-3-ol The oily acetal, as obtained in Description 4, was dissolved in dioxan (2 ml) and treated with 2.5M HCl (1 ml). After 30 minutes the reaction was diluted with ether and neutralised with sodium carbonate solution.

The two phases were separated, the aqueous layer further extracted with ether and the combined extracts washed with water and brine and dried over sodium sulphate. The organic phase was filtered and applied to Kieselgel 60 (10 g) and diluted with ethyl acetate-heptane-triethyl- amine (10:20:2). Three fractions were obtained (total 128 g) containing the title compound. TLC (silica gel; ethyl acetate-heptane-triethylamine (10:20:2) showed the presence of varying amounts of the two positional isomers in each fraction.

IR (KBr disc) 3450, 2230 cm$^{-1}$ for all three fractions.

Mass spectrum (Isobutane and ammonium C.I.) showed m/$_z$ 271 (MH$^+$ — H$_2$O) for all three fractions.

DESCRIPTION 6

6-Cyano-3,4-dihydro-2,2-dimethyl-trans-4-(2-oxo-1-pyrrolidinyl)-2H-benzo[b]pyran-3ol 6-Cyano-3,4-dihydro-2,2-dimethyl-3,4-epoxy-2H-benzo[b]pyran (0.50 g), as obtained in Description 1, 4-aminobutyric acid (1.25 g) and sodium bicarbonate (1.00 g) were refluxed in ethanol (15 cc) and distilled water (2.5 cc) for 10 hours. The reaction was filtered and evaporated and the residue chromatographed on 25 g Kieselgel 60. Elution with MeOH-chloroform (1:3) gave 132 mg of the most polar product. This was refluxed in toluene (10 cc) for 2 hours, cooled and the solvent evaporated. The residue was chromatographed on 5 g Kieselgel 60 and eluted with MeOH-chloroform (1:3) to give the title compound as a white solid (90 mg), m.p. 230°-231°.

IR (KBr disc): 3260, 2220, 1651 cm$^{-1}$;

NMR (CDCl$_3$): 1.28 (3H; 1.55 (3H); 2.11 (2H, m); 2.57 (2H, m); 3.22 (3H, 1 exchangeable H, broad m); 3.64 (1H, d, J=10; 5.26 (1H, d, J=10); 6.87 (1H, d, J=9; 7.24 (1H, narrow m); 7.45 (1H, q, J=9, 2);

Analysis calculated for C$_{16}$H$_{18}$N$_2$O$_3$: C, 67.12; H, 6.34; N, 9.78%. Found: C, 66.83; H, 6,17; N, 9.50%.

DESCRIPTION 7

6-Cyano-3,4-dihydro-2,2-dimethyl-trans-4-(2-oxo-1-pyrrolidinyl)-2H-benzo[b]pyran-3-ol 6-Cyano-3,4-dihydro-2,2-dimethyl-3,4-epoxy-2H-benzo[b]pyran (1.00 g), as obtained in Description 1, ethyl-4-aminobutyrate hydrochloride (0.84 g), ethanol (50 ml) and sodium hydroxide pellets (0.20 g) were stirred at room temperature for 8 days, then at 40< for 3 hours. After cooling and evaporation the residue was taken up in ethyl acetate and filtered. Evaporation of the filtrate gve a gum (1.46 g) which was chromotographed using a chromatotron (2 mm silica gel HF$_{254}$ plate; 2 runs; solvent flow rate 6 ml/min.). Elution with 2% methanol-chloroform mixture gave starting epoxide (0.23 g) followed by a more polar ester fraction (0.64 g), and a mixture (0.15 g) which on further chromatography under identical conditions gave 6-cyano-3,4-dihydro-2,2-dimethyl-trans-4-(2oxo-1-pyrrolidinyl)-2H-benzo[b]pyran-3-ol having an identical NMR spectrum to that obtained in Description 6.

A portion of the ester fraction (150 mg) was dissolved in ether containing a little ethanol and treated with anhydrous ethanolic HCl. The precipitate was collected and triturated with ether to give trans-4-(3-carbethoxypropylamino)-6-cyano-2,2-dimethyl-2H-benzo[b]pyran-3-ol hydrochloride (138 mg) of m.p. 198°-200°.

NMR (CD$_3$OD): 1.23 (s, 3H) overlapped with; 1.26 (t, J=8, 8 3H); 1.58 (s, 3H); 2.19 (m, 2H); 2.53 (m, 2H); 2.85-3.45 (irreg. m, 2H); 4.02 (d, J=10, 1H) overlapped with 4.16 (q, J=8, 8, 8 2H) and 3.75-4.65 (m, 3H, exchangeable); 4.53 (3, J=10, 1H); 7.00 (d, J=9, 1H); 7.60 (q, J=9, 2, 1H); 8.15 (d, J=2, 1H).

Analysis calculated for C$_{18}$H$_{25}$N$_2$O$_4$: C, 58.61; H, 6.83; N, 7.59%. Found: C, 58.55; H, 6.80; N, 7.29%.

The remainder of the ester fraction was heated under reflux in xylene (50 ml) for 7.25 hours. The solution was cooled and filtration gave 6-cyano-3,4-dihydro-2,2-dimethyl-trans-4-(2-oxo-1-pyrrolidinyl)-2H-benzo[b]-pyran-3ol (425 mg) as crystals of m.p. 226° having an identical NMR spectrum and t.l.c. characteristics as the compound of Description 6.

DESCRIPTION 8

6-Cyano-3,4-dihydro-2,2-dimethyl-trans-4-(2-oxo-1-pyrrolidinyl)-2H-benzo[b]pyran-3-ol 6-Cyano-3,4-dihydro-2,2-dimethyl-trans-4-(1-keto-4-chlorobutylamino)-2H-benzo[b]pyran-3-ol (0.76 g), as obtained in Description 3, in dry tetrahydrofuran (10 ml) was added to a suspension of sodium hydride (0.15 g) in tetrahydrofuran (20 ml) and the reaction stirred under nitrogen for 3 hours. Addition of water and extraction via ethyl acetate gave 540 mg of the title compound having an identical NMR spectrum and tlc characteristics as the compound of Description 6.

DESCRIPTION 9

6-Cyano-3,4-dihydro-2,2-dimethyl-trans-4-(2-oxo-1-pyrrolidinyl)-2H-benzo[b]pyran-3-ol A solution of 6-cyano-3,4-dihydro-2,2-dimethyl-trans-3-bromo-4-hydroxy-2H-benzo[b]pyran (4 g, 14.2 mM) in dimethylsulphoxide (20 ml) was stirred and sodium hydride (60% dispersion in oil, 0.6 g, 15 mM) added. The suspension was stirred for 1 hour when a solution of 6-cyano-3,4-dihydro-2,2-dimethyl-3,4-epoxy-2H-benzo[b]pyran resulted. 2-Pyrrolidone (1.8 g, 21 mM) and further sodium hydride (0.8 g, 21 mM) were introduced and the mixture stirred at room temperature for an additional 16 hours. Water (40 ml) was slowly added to the mixture to induce crystallisation of the product after which it was cooled in ice and filtered under suction. Crystallisation from ethanol (20 ml) gave the title compound as a cream coloured solid in 60% yield. Recrystallisation from ethyl acetate afforded the pure product as needles, m.p. 226.5°-227.5° having an nmr spectrum and t.l.c. characteristics identical to those of the compound of Description 6.

DESCRIPTION 10

6-Cyano-3,4-dihydro-2,2-dimethyl-trans-4-(2-oxo-1-pyrroldinyl)-2H-benzo[b]pyran-3-ol 6-Cyano-3,4-dihydro-2,2-dimethyl-trans-4-(2-hydroxy-1-pyrrolidinyl)-2H-benzo[b]pyran-3-ol (5 mg), as obtained in Description 5, dissolved in methanol-water (1 ml) was treated with an excess of sodium periodate with stirring during 15 hours at room temperature. Evaporation of solvents and extraction by ethyl acetate gave material having identical thin layer characteristics when applied to silica gel plates developed in either chloroform-methanol (15:1) or heptane-ethyl acetate-triethylamine and infra red spectrum on the compound of Description 6.

DESCRIPTION 11

6-Cyano-3,4-dihydro-2,2-dimethyl-trans-4-(2-oxo-1-piperidinyl)-2H-benzo[b]pyran-3-ol 6-Cyano-3,4-dihydro-2,2-dimethyl-3,4-epoxy-2H-benzo[b]pyran and 2-piperidone was stirred in dimethyl sulphoxide under nitrogen at room temperature. Sodium hydride (81% dispersion in mineral oil) was added during 5 mins. and the reaction stirred for a further 6 hours. Addition of water, extraction with ethyl acetate, drying of the organic phase with magnesium sulpate, filatration, evaporation and recrystallisation from ethyl acetate gave 6-cyano-3,4-dihydro-2, 2-dimethyl-trans-4-(2-oxo-1-piperidinyl)-2H-benzo[b]pyran-3-ol was prepared, as crystals of m.p. 155° C.

IR (KBr disc) 3480, 2212, 1612 cm$^{-1}$;

NMR (CDCl$_3$ soln): 1.25 (3H, s); 1.50 (3H, s); 1.63-2.10 (4H, m); 2.36-2.76 (2H, m); 3.72 (1H, d, J=10 Hz); 3.90-4.20 (1H, exchangeable, m); 5.72 (1H, d, J=10 Hz); 6.76 (1H, d, J=8 Hz); 7.17 (1H, m, narrow); 7.42 (1H, q, J=8, 2 Hz).

DESCRIPTION 12

6-Chloro-3,4-dihydro-2,2-dimethyl-trans-3-bromo-4-hydroxy-2H-benzo[b]pyran

The title compound was prepared analogously to the preparation of the 3-bromo-4-hydroxy compound of Description 1 giving a crude crystalline solid.

NMR (CDCl$_3$): 1.35 (3H, s); 1.53 (3H, s); 3.22 (1H, m); 4.00 (1H, d, J=9 Hz); 4.77 (1H, d, J=9 Hz); 6.51 (1H, d, J=8 Hz); 7.03 (1H, q, J=8.2 Hz); 7.30 (1H, narrow m).

DESCRIPTION 13

6-Chloro-3,4-dihydro-2,2-dimethyl-3,4-epoxy-2H-benzo[b]pyran

The crude crystalline solid (10.27 g) of Description 12 was dissolved in dimethyl sulphoxide (50 ml) and treated with sodium hydride (1.06 g, 80% dispersion on oil) over a period of an hour. The resulting material was used as such immediately in Description 13.

DESCRIPTION 14

6-Chloro-3,4-dihydro-2,2-dimethyl-trans-4-(2-oxo-1-pyrrolidinyl)-2H-benzo[b]pyran-3-ol 2-Pyrrolidone (4.5 g) and sodium hydride (1.59 g) were added to the material of Description 13, and the mixture stirred for 20 hours. Cautious addition of water and filtration of the resulting solid, followed by two crystallisations from ethyl acetate gave the title compound, m.p. 202°–203°.

DESCRIPTION 15

6-Acetyl-3,4-dihydro-2,2-dimethyl-trans-4-(2-oxo-1-pyrrolidinyl)-2H-benzo[b]pyran-3-ol 6-Acetyl-3,4-dihydro-2,2-dimethyl-3,4-epoxy-2H-benzo[b]pyran (0.33 g, prepared as described in Example 1 of U.K. Pat. No. 1,511,187), and 2-pyrrolidone (0.15 g), were stirred in dimethylsulphoxide (25 ml) under nitrogen at room temperature. Sodium hydride (0.05 g, 80%) was added during 2 mins and the reaction stirred for a further 22 hours. Addition of water, extraction with ethyl acetate, drying of the organic layer with magnesium sulphate, filtration, evaporation and recrystallisation from ethyl acetate gave the title compound (0.04 g) of m.p. 218°–219°.

NMR (CDCl$_3$: 1.32 (3H, s); 1.55 (3H, s); 1.85–2.25 (2H, m); 2.55 (3H, s) overlapped by 2.45–2.75 (2H, m); 2.80–3.45 (3H, m); 3.75 (1H, d, J=10 Hz); 5.36 (1H, d, J=10 Hz); 6.96 (1H, d, J=8 Hz); 7.63 (1H, narrow m); 7.83 (1H, q, J=8, 2 Hz).

EXAMPLE 1

6-Cyano-2,2-dimethyl-4-(2-oxo-1-pyrrolidinyl)-2H-1-benzopyran

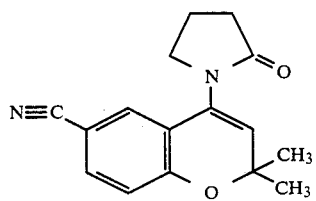

(1)

Sodium hydride (114 mg., 80% dispersion in oil) was added to a solution of trans-6-cyano-2,2-dimethyl-4-(2-oxo-1-pyrrodinyl)-2H-1-benzopyran-3-ol (310 mg) in anhydrous tetrahydrofuran (12 ml) and the mixture stirred and heated under reflux for 16 hr. The mixture was cooled and concentrated. Cautious addition of water was followed by ethyl acetate extraction. The ethyl acetate was washed with water until the washings were neutral, dried and evaporated to leave a gum. Recrystallisation from ethyl acetate gave the title compound (100 mg) as prisms of m.p. 143–144.

NMR (CDCL$_3$): δ 1.50 (S, 6H); 2.22–2.58 (m, 4H); 3.61 (t, J=7, 7H$_z$, 2H); 5.67 (S, 1H); 6.85 (d, J=8, 1H); 7.19 (3, J=2, 1H); 7.42 (q, J=8, 2, 1H).

EXAMPLE 2

6-Cyano-2,2-dimethyl-4-(2-oxo-1-piperidinyl)-2H-1-benzopyran

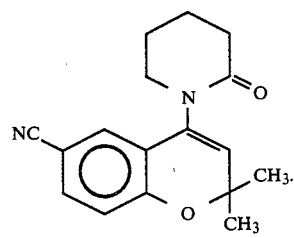

(2)

Sodium hydride (170 mg, 80% dispersion in oil) was added to a solution of trans-6-cyano-3,4-dihydro-2,2-dimethyl-4-(2-oxo-1-piperidinyl)-2H-1-benzopyran-3-ol (1.65 g) in anhydrous tetrahydrofuran (25 ml) and the reaction mixture stirred and heated under reflux for 48 hours. Work up as in Example 1, followed by chromatography (chromatotron—2 mm Silica gel HF$_{254}$—elution with ethyl acetate at 6 ml/min) gave one fraction (312 mg) which on recrystallisation from ethyl acetate gave the title compound as crystals (66 mg) of m.p. 162°–163° C.

NMR (CDCl$_3$): δ 1.27 (s, 6H); 1.47–1.87 (m, 4H); 2.10–2.41 (m, 2H); 3.00–3.36 (m, 2H); 5.40 (s, 1H); 6.56 (d, J=8, 1H); 6.87 (d, J=3, 1H); 7.14 (q, J=8, 3 Hz, 1H).

Anal. Calcd. for $C_{17}H_{18}N_2O_2$: C, 72.32; H, 6.43; N, 9.92. Found: C, 72.45; H, 6.69; N, 9.73.

EXAMPLE 3

2,2-dimethyl-6-nitro-4-(2-oxo-1-pyrrolidinyl)-2H-1-benzopyran

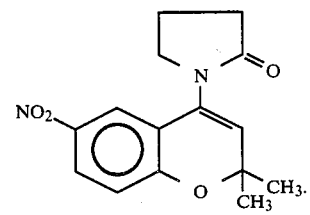

(3)

The title compound was prepared in similar fashion from trans-3,4-dihydro-2,2-dimethyl-6-nitro-4-(2-oxo-1-pyrrolidinyl)-2H-1-benzopyran-3-ol giving yellow prisms, m.p. 135°–137° C.

NMR (CDCl$_3$): δ 1.54 (s, 6H); 2.10–2.73 (m, 4H); 3.64 (t, J=7, 7 Hz, 2H); 5.73 (s, 1H); 6.90 (d, J=9 Hz, 1H); 7.84 (d, J=3 Hz, 1H); 8.08 (q, J=9, 3 Hz, 1H).

EXAMPLE 4

6-Chloro-2,2-dimethyl-4-(2-oxo-1-pyrrolidinyl)-2H-1-benzopyran

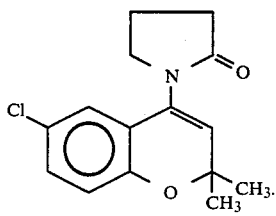
(4)

The title compound was prepared in similar fashion from trans-6-chloro-3,4-dihydro-2,2-dimethyl-4-(2-oxo-1-pyrrolidinyl)-2H-1-benzopyran-3-ol giving prisms, m.p. 123°–125° C.

NMR (CDCl$_3$): δ 1.48 (s, 6H); 2.05-2.70 (m, 4H); 3.61 (t, J=7, 7 Hz, 2H); 5.67 (s, 1H); 6.78 (d, J=9, 1H); 6.91 (d, J=3, 1H); 7.13 (q, J=9, 3 Hz, 1H).

EXAMPLE 5

6-Acetyl-2,2-dimethyl-4-(2-oxo-1-pyrrolidinyl)-2H-1-benzopyran

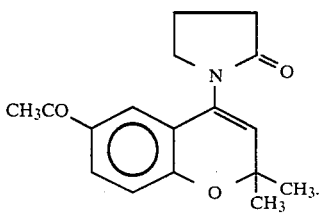
(5)

The title compound was prepared in similar fashion from trans-6-acetyl-3,4-dihydro-2,2-dimethyl-4-(2-oxo-1-pyrrolidinyl)-2H-1-benzopyran-3-ol giving colourless prisms, m.p. 106°–108° C.

NMR (CDCl$_3$): δ 1.50 (s, 6H); 2.10-2.70 (m, 4H); 2.52 (s, 3H); 3.62 (t, J=7, 7 Hz, 2H); 5.68 (s, 1H); 6.86 (d, J=9 Hz, 1H); 7.58 (d, J=2 Hz, 1H); 7.79 (q, J=9, 2 Hz, 1H).

EXAMPLE 6

6-Cyano-3,4-dihydro-2,2-dimethyl-4-(1-2-oxo-pyrrolidinyl)-2H-1-benzopyran

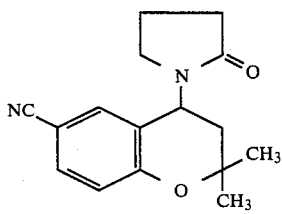
(6)

The compound of example 1 (0.83 g) and 10% palladium/charcoal (80 mg) were shaken in ethyl acetate (30 ml) for 32 hours in an atmosphere of hydrogen at room temperature. Filtration and evaporation of solvent gave a mixture (0.80 g) which was treated with N-bromosuccinimide (0.7 g) and water (0.5 ml) in dimethyl sulphoxide (30 ml) during 0.5 hr. at room temperture. Addition of water and extraction via ethyl acetate, drying over anhydrous magnesium sulphate, filtration and evaporation gave a crude gum (0.9 g). The product of two such runs (1.8 g) was chromographed in silica gel (44 g). Elution with ethyl acetate gave, in the later fractions, a solid (0.78 g) which was recrystallised from ethyl acetatepentane to give the title compound (0.68 g) as colourless needles of m.p. 133°–135° C.

NMR (CDCl$_3$): δ 1.36 (s 3H); 1.49 (s, 3H); 1.93 (d, J=9 Hz 2H) overlapping signal centred at 2.12 (m, 2H); 2.40-2.58 (m, 2H); 2.90-3.40 (m, 2H); 5.53 (t, J=9 Hz, 1H); 6.87 (d, J=8 Hz, 1H); 7.28 (irreg narrow m, 1H); 7.45 (m, 1H).

IR (KBr disc) 2220, 1675 cm$^{-1}$.

The following compounds are prepared analogously to the methods described in examples 1–5:

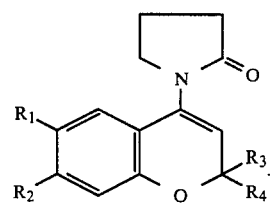

| Compound No. | R$_1$ | R$_2$ | R$_3$ | R$_4$ |
|---|---|---|---|---|
| 7 | NO$_2$ | H | CH$_3$ | H |
| 8 | H | NO$_2$ | CH$_3$ | CH$_3$ |
| 9 | H$_2$N | NO$_2$ | CH$_3$ | CH$_3$ |
| 10 | NO$_2$ | NH$_2$ | CH$_3$ | CH$_3$ |

Pharmacological Data

Systolic blood pressures were recorded by a modification of the tail cuff method described by I M Claxton, M G Palfreyman, R H Poyser, R L Whiting, European Journal of Pharmacology, 37, 179 (1976). W+W BP recorder, model 8005, was used to display pulses, Prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive

| Compound of Example 1 | Time Post Dose Hours | % Change in Systolic Blood Pressure | % Change in Heart Rate |
|---|---|---|---|
| 6 rats | 1 | −47 ± 5 | −3 ± 3 |
| Dose 0.3 mg/kg po | 2 | −30 ± 1 | −3 ± 2 |
| Initial Blood Pressure | 4* | −21 ± 3 | −8 ± 2 |
| 2.20 ± 4 mmHg | 6 | −16 ± 3 | −9 ± 3 |
| Initial Heart Rate | 24 | −3 ± 3 | −5 ± 2 |
| 482 ± 15 beats/min | | | |

*1 rat had no measurable pulse

Compounds 2 to 5 are also found to show blood pressure lowering activity in this test.

Toxicity

No toxic effects were observed in the above test.

We claim:
1. Trans-3,4-dihydro-2,2-dimethyl-6-nitro-4-(2-oxopyrrolidinyl)-2H-1-benzopyran-3-ol.

* * * * *